(12) United States Patent
Kappetein et al.

(10) Patent No.: US 11,633,281 B2
(45) Date of Patent: Apr. 25, 2023

(54) IMPLANTABLE COAPTATION ASSIST DEVICES WITH SENSORS AND ASSOCIATED SYSTEMS AND METHODS

(71) Applicants: Half Moon Medical, Inc., Menlo Park, CA (US); Medtronic, Inc., Minneapolis, MN (US)

(72) Inventors: Arie Pieter Kappetein, Rotterdam (NL); James I. Fann, Portola Valley, CA (US); Hanson S. Gifford, III, Woodside, CA (US); Matthew McLean, San Francisco, CA (US); Gaurav Krishnamurthy, Mountain View, CA (US); Neil Zimmerman, Menlo Park, CA (US)

(73) Assignees: Half Moon Medical, Inc., Menlo Park, CA (US); Medtronic, Inc., Minneapolis, MN (US)

( * ) Notice: Subject to any disclaimer, the term of this patent is extended or adjusted under 35 U.S.C. 154(b) by 398 days.

(21) Appl. No.: 16/745,246

(22) Filed: Jan. 16, 2020

(65) Prior Publication Data

US 2020/0222185 A1    Jul. 16, 2020

Related U.S. Application Data

(60) Provisional application No. 62/793,273, filed on Jan. 16, 2019.

(51) Int. Cl.
  *A61F 2/24*   (2006.01)
  *A61B 5/0215*   (2006.01)
  (Continued)

(52) U.S. Cl.
  CPC ............ *A61F 2/2442* (2013.01); *A61B 5/029* (2013.01); *A61B 5/0215* (2013.01);
  (Continued)

(58) Field of Classification Search
  CPC .. A61F 2/2442; A61F 2/90; A61F 2/24; A61B 5/0215; A61B 5/029; A61B 5/4851
  (Continued)

(56) References Cited

U.S. PATENT DOCUMENTS 6,869,444 B2    3/2005  Gabbay
7,160,322 B2    1/2007  Gabbay
(Continued)

FOREIGN PATENT DOCUMENTS

EP    2819618 A1    1/2015
EP    3167846 A1    5/2017
(Continued)

OTHER PUBLICATIONS

ISA, PCT Application No. PCT/US2018/043566, International Search Report and Written Opinion dated Oct. 24, 2018, 14 pages.
(Continued)

*Primary Examiner* — Suzette J Gherbi
(74) *Attorney, Agent, or Firm* — Perkins Coie LLP (57) ABSTRACT

Coaptation assist device for repairing cardiac valves and associated systems and methods are disclosed herein. A coaptation assist device configured in accordance with embodiments of the present technology can include, for example, a fixation member configured to press against cardiac tissue proximate to a native valve annulus, and a stationary coaptation structure extending away from the fixation member. The coaptation structure can include an anterior surface configured to coapt with a first native leaflet during systole and a posterior surface configured to displace at least a portion of a second native leaflet. The device also includes at least one sensor configured to detect parameters associated with at least one of cardiac function and device
(Continued)

functionality. The sensors can be pressure sensors configured to detect left atrial pressure and/or left ventricular pressure.

24 Claims, 7 Drawing Sheets

(51) Int. Cl.
  *A61B 5/029* (2006.01)
  *A61B 5/00* (2006.01)
  *A61F 2/90* (2013.01)
(52) U.S. Cl.
  CPC ............ *A61B 5/4851* (2013.01); *A61B 5/686* (2013.01); *A61F 2/90* (2013.01); *A61F 2210/0014* (2013.01)
(58) Field of Classification Search
  USPC .................................................. 623/2.1–2.19
  See application file for complete search history.

(56) References Cited

U.S. PATENT DOCUMENTS

| | | | |
|---|---|---|---|
| 8,545,553 | B2 | 10/2013 | Zipory et al. |
| 8,574,290 | B2 | 11/2013 | Alameddine |
| 8,821,570 | B2 | 9/2014 | DuMontelle et al. |
| 8,845,722 | B2 | 9/2014 | Gabbay |
| 9,011,523 | B2 | 4/2015 | Sequin |
| 9,592,118 | B2 | 3/2017 | Khairkhahan et al. |
| 9,592,121 | B1 | 3/2017 | Khairkhahan |
| 9,610,163 | B2 | 4/2017 | Khairkhahan et al. |
| 9,907,652 | B2 | 3/2018 | Chau et al. |
| 10,123,874 | B2 | 11/2018 | Khairkhahan et al. |
| 10,166,098 | B2 | 1/2019 | Khairkhahan et al. |
| 10,390,714 | B2 * | 8/2019 | Wolinsky ............ A61B 5/02152 |
| 10,408,690 | B2 | 9/2019 | Gouko et al. |
| 10,449,046 | B2 | 10/2019 | Rafiee |
| 10,470,883 | B2 | 11/2019 | Khairkhahan et al. |
| 10,478,303 | B2 | 11/2019 | Khairkhahan |
| 10,500,048 | B2 | 12/2019 | Khairkhahan et al. |
| 10,512,542 | B2 | 12/2019 | Khairkhahan et al. |
| 10,531,956 | B2 | 1/2020 | Skarsgard |
| 10,702,386 | B2 | 7/2020 | Khairkhahan et al. |
| 11,000,372 | B2 * | 5/2021 | Khairkhahan ........ A61F 2/2463 |
| 11,083,572 | B2 * | 8/2021 | McLean .................. A61F 2/246 |
| 11,344,410 | B2 * | 5/2022 | Hacohen ............... A61F 2/2418 |
| 2003/0199975 | A1 | 10/2003 | Gabbay |
| 2004/0093060 | A1 | 5/2004 | Sequin et al. |
| 2007/0038297 | A1 | 2/2007 | Bobo, Jr. et al. |
| 2008/0077235 | A1 | 3/2008 | Krison |
| 2010/0217382 | A1 | 8/2010 | Chau et al. |
| 2010/0262233 | A1 | 10/2010 | He |
| 2012/0197388 | A1 | 8/2012 | Khairkhahan et al. |
| 2013/0006352 | A1 | 1/2013 | Yaron |
| 2014/0067048 | A1 | 3/2014 | Chau et al. |
| 2014/0358223 | A1 | 12/2014 | Rafiee et al. |
| 2015/0119981 | A1 | 4/2015 | Khairkhahan et al. |
| 2015/0142104 | A1 | 5/2015 | Braido |
| 2015/0148893 | A1 | 5/2015 | Braido et al. |
| 2015/0230919 | A1 | 8/2015 | Chau et al. |
| 2015/0327996 | A1 | 11/2015 | Fahim et al. |
| 2016/0030176 | A1 | 2/2016 | Mohl et al. |
| 2016/0045165 | A1 * | 2/2016 | Braido ............ A61B 17/12122 623/2.1 |
| 2016/0074164 | A1 | 3/2016 | Naor |
| 2017/0095332 | A1 | 4/2017 | Bruchman |
| 2017/0165067 | A1 | 6/2017 | Barajas-Torres et al. |
| 2017/0258589 | A1 | 9/2017 | Pham et al. |
| 2017/0296706 | A1 | 10/2017 | Simon et al. |
| 2018/0147054 | A1 | 5/2018 | Chau et al. |
| 2018/0188108 | A1 | 6/2018 | Grimm et al. |
| 2018/0243087 | A1 | 8/2018 | Kapadia |
| 2018/0271651 | A1 | 9/2018 | Christianson et al. |
| 2020/0205978 | A1 | 7/2020 | Padala et al. |
| 2020/0268512 | A1 | 8/2020 | Mohl |
| 2020/0289265 | A1 * | 9/2020 | Gifford, III ........... A61F 2/2463 |
| 2020/0360138 | A1 * | 11/2020 | Ma ........................ A61F 2/2418 |
| 2021/0085462 | A1 * | 3/2021 | Gifford, III ............. A61F 2/246 |
| 2021/0307901 | A1 * | 10/2021 | Raanani ................ A61F 2/2436 |
| 2022/0039951 | A1 * | 2/2022 | Khairkhahan ........ A61F 2/2454 |
| 2022/0125579 | A1 * | 4/2022 | McLean ................. A61F 2/246 |
| 2022/0125586 | A1 * | 4/2022 | Rafiee .................... A61F 2/2436 |
| 2022/0160508 | A1 * | 5/2022 | Miyashiro ............. A61F 2/2466 |

FOREIGN PATENT DOCUMENTS

| | | | | |
|---|---|---|---|---|
| WO | 2005002424 | A3 | 1/2005 | |
| WO | 2012177942 | A2 | 12/2012 | |
| WO | 2014195422 | A1 | 12/2014 | |
| WO | 2014207575 | A2 | 12/2014 | |
| WO | 2018142186 | A1 | 8/2018 | |
| WO | 2019045910 | A1 | 3/2019 | |
| WO | 2020101676 | A1 | 5/2020 | |
| WO | WO-2021113449 | A1 * | 6/2021 | ........... A61B 5/0031 |

OTHER PUBLICATIONS

ISA, PCT Application No. PCTUS2018/061126, International Search Report and Written Opinion dated Jul. 9, 2019, 12 pages.
ISA, PCT Application No. PCT/US2020/013953, International Search Report and Written Opinion dated Apr. 15, 2020, 14 pages.
ISA, PCT Application No. PCT/US2020/022471, International Search Report and Written Opinion dated Jun. 3, 2020, 17 pages.
ISA, PCT Application No. PCT/US2020/051887, International Search Report and Written Opinion dated Nov. 27, 2020, 13 pages.

* cited by examiner

IMPLANTABLE COAPTATION ASSIST DEVICES WITH SENSORS AND ASSOCIATED SYSTEMS AND METHODS

CROSS-REFERENCE TO RELATED APPLICATION(S)

This application claims priority to and the benefit of U.S. Provisional Application No. 62/793,273, filed Jan. 16, 2019, which is incorporated herein by reference in its entirety.

TECHNICAL FIELD

The present technology relates generally to valve repair devices. In particular, several embodiments are directed to implantable coaptation assist devices with sensors and associated systems and methods.

BACKGROUND

Conditions affecting the proper functioning of the mitral valve include, for example, mitral valve regurgitation, mitral valve prolapse and mitral valve stenosis. Mitral valve regurgitation is a disorder of the heart in which the leaflets of the mitral valve fail to coapt into apposition at peak contraction pressures, resulting in abnormal leaking of blood from the left ventricle into the left atrium. There are several structural factors that may affect the proper closure of the mitral valve leaflets. For example, many patients suffering from heart disease have an enlarged mitral annulus caused by dilation of heart muscle. Enlargement of the mitral annulus makes it difficult for the leaflets to coapt during systole. A stretch or tear in the chordae tendineae, the tendons connecting the papillary muscles to the inferior side of the mitral valve leaflets, may also affect proper closure of the mitral annulus. A ruptured chordae tendineae, for example, may cause a valve leaflet to prolapse into the left atrium due to inadequate tension on the leaflet. Abnormal backflow can also occur when the functioning of the papillary muscles is compromised, for example, due to ischemia. As the left ventricle contracts during systole, the affected papillary muscles do not contract sufficiently to effect proper closure.

Mitral valve prolapse, or when the mitral leaflets bulge abnormally up in to the left atrium, causes irregular behavior of the mitral valve and may also lead to mitral valve regurgitation. Normal functioning of the mitral valve may also be affected by mitral valve stenosis, or a narrowing of the mitral valve orifice, which causes impedance of filling of the left ventricle in diastole.

Mitral valve regurgitation is often treated using diuretics and/or vasodilators to reduce the amount of blood flowing back into the left atrium. Other treatment methods, such as surgical approaches (open and intravascular), have also been used for either the repair or replacement of the valve. For example, typical repair approaches have involved cinching or resecting portions of the dilated annulus.

Cinching of the annulus has been accomplished by the implantation of annular or peri-annular rings which are generally secured to the annulus or surrounding tissue. Other repair procedures have also involved suturing or clipping of the valve leaflets into partial apposition with one another.

Alternatively, more invasive procedures have involved the replacement of the entire valve itself where mechanical valves or biological tissue are implanted into the heart in place of the mitral valve. These invasive procedures are conventionally done through large open thoracotomies and are thus very painful, have significant morbidity, and require long recovery periods.

With many repair and replacement procedures, however, the durability of the devices or improper sizing of annuloplasty rings or replacement valves may result in additional problems for the patient. Moreover, many of the repair procedures are highly dependent upon the skill of the cardiac surgeon where poorly or inaccurately placed sutures may affect the success of procedures.

Compared to other cardiac valves, portions of the mitral valve annulus have limited radial support from surrounding tissue and the mitral valve has an irregular, unpredictable shape. For example, the inner wall of the mitral valve is bound by only a thin vessel wall separating the mitral valve annulus from the inferior portion of the aortic outflow tract. As a result, significant radial forces on the mitral annulus could lead to collapse of the inferior portion of the aortic tract with potentially fatal consequences. The chordae tendineae of the left ventricle are often an obstacle in deploying a mitral valve repair device. The maze of chordae in the left ventricle makes navigating and positioning a deployment catheter that much more difficult in mitral valve repair. Given the difficulties associated with current procedures, there remains the need for simple, effective, and less invasive devices and methods for treating dysfunctional heart valves.

BRIEF DESCRIPTION OF THE DRAWINGS

Many aspects of the present disclosure can be better understood with reference to the following drawings. The components in the drawings are not necessarily to scale, and instead emphasis is placed on illustrating clearly the principles of the present disclosure. For ease of reference, throughout this disclosure identical reference numbers and/or letters are used to identify similar or analogous components or features, but the use of the same reference number does not imply that the parts should be construed to be identical. Indeed, in many examples described herein, identically numbered components refer to different embodiments that are distinct in structure and/or function. The headings provided herein are for convenience only.

DETAILED DESCRIPTION

Implantable coaptation assist devices with sensors and associated systems and methods are disclosed herein. In some embodiments, for example, a coaptation assist device (also referred to as a "mitral valve repair device") includes (a) a coaptation structure that takes the place of a native leaflet and coapts with one or more opposing native leaflets during systole, and (b) one or more sensors that monitor various physiological and/or device parameters that can be used to dictate or guide patient care. As such, the present technology may be referred to as a "smart" heart valve repair device. Specific details of several embodiments of the technology are described below with reference to FIGS. 1A-5B. Although many of the embodiments are described below with respect to implant devices, systems, and methods for repair of a native mitral valve, other applications and other embodiments in addition to those described herein are within the scope of the technology. For example, the present technology may be used at other target sites, like the tricuspid valve. Additionally, several other embodiments of the technology can have different configurations, components, or procedures than those described herein, and that features of the embodiments shown can be combined with one another. A person of ordinary skill in the art, therefore, will accordingly understand that the technology can have other embodiments with additional elements, or the technology can have other embodiments without several of the features shown and described below with reference to FIGS. 1A-5B.

With regard to the terms "distal" and "proximal" within this description, unless otherwise specified, the terms can reference a relative position of the portions of a valve repair device and/or an associated delivery device with reference to an operator and/or a location in the vasculature or heart. For example, in referring to a delivery catheter suitable to deliver and position various valve repair devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a heart valve repair device, the terms "proximal" and "distal" can refer to the location of portions of the device with respect to the direction of blood flow. For example, proximal can refer to an upstream position or a location where blood, during its typical, non-regurgitating path, flows toward the device (e.g., inlet region of the native valve), and distal can refer to a downstream position or a location where blood flows away the device (e.g., outflow region of the native valve).

Overview

The present technology includes devices for treating mitral valve regurgitation that places a coaptation structure (also referred to as a "baffle") over a portion of a native valve leaflet to address regurgitation caused by dilation of the annulus or deterioration of the native leaflet. The coaptation structure fills at least a portion of the space taken by the closed native leaflet and extends beyond that space to re-establish coaptation with the surrounding leaflets. For example, the coaptation structure may extend in front of a central portion of the posterior leaflet (i.e., P2 of the posterior leaflet), pushing the posterior leaflet back toward the ventricular wall, such that the coaptation structure is positioned to coapt with the anterior leaflet during systole. The coaptation structure is retained in place by a fixation member (also referred to as an "anchoring member" or "brim") configured to anchor to cardiac tissue of the left atrium which surrounds the mitral annulus. The fixation member can be an expandable nitinol mesh tube (e.g., a stent) that shaped to conform to the walls of the left atrium just above the mitral annulus. In various embodiments, the fixation member may also or alternatively include portions that press against and anchor to sub-annular tissue. In some embodiments, the fixation member has cleats or other frictional elements to hold it in place against the atrial wall. Over a period after implantation (e.g., 3 days, 2 weeks, 1 month, 2 months), the fixation member or portions thereof become covered by a layer of tissue, and this tissue ingrowth adheres it permanently to the atrial wall. The device can further include one or more clips that extend from the fixation member and/or the coaptation structure to a position behind individual mitral valve leaflets to the sub-annular space for further stabilization of the implant. In some embodiments, for example, the device includes a clip that reaches under the P2 or other portion of the posterior leaflet up to the sub-annular space and further stabilizes the implant. Further descriptions of implant devices with coaptation assist devices are also described in International Patent Application No. PCT/US2018/043566, filed Jul. 24, 2018, and in International Patent Application No. PCT/US2018/061126, filed Nov. 14, 2018, each of which is incorporated by reference in its entirety.

The mitral repair device includes at least one sensor (also referred to as a "sensing component") for detecting parameters associated with cardiac function, other physiological parameters, and/or device functionality to provide real-time monitoring of the detected parameters. The sensor can include a pressure sensor, an accelerometer, a strain gauge, an acoustic sensor (e.g., a microphone), a flow sensor, a temperature sensor, and/or other type of sensing mechanism. The sensor can be communicatively coupled to a communication component or transmitter, such as an antenna, that wirelessly transmits the detected measurements to an external computing device outside the body. From the external computing device and/or a device communicatively coupled thereto, the data can be displayed and/or further analyzed via software techniques (e.g., compared against threshold values, interpreted to determine related parameters). The sensor can be powered via an external source and/or with a battery or capacitive element integrated into the device or sensor itself.

Since the mitral repair device includes portions that, when implanted, reside in both the atrium and the ventricle, the mitral valve repair device can include sensors in both the atrium and the ventricle to provide real-time monitoring and wireless communication of parameters associated with both locations, such as atrial pressure and ventricular pressure. When the mitral valve repair device includes a pressure sensor (e.g., a capacitive pressure microsensor) in the atrial region (e.g., on or extending from the fixation member), the device can detect left atrial pressure ("LAP"). The monitoring of LAP may be of particular interest because of the potential for pressure-guided management of congestive heart failure ("CHF"). Many patients suffering from mitral valve disease also have CHF, which may be a result of the untreated mitral regurgitation or other conditions that damage or weaken the heart, such as coronary artery disease and heart attack, high blood pressure, cardiomyopathy, heart arrhythmias, and other chronic disease. The real-time monitoring of parameters, such as LAP and/or pulmonary artery pressure, via the sensor device allows the clinician to effectively manage CHF patients and catch worsening conditions before the onset of symptoms. LAP monitoring can also provide a way to monitor proper device function as it relates to the elimination of mitral regurgitation (i.e., increased regurgitation would cause increased LAP).

When the mitral valve repair device includes a pressure sensor in the ventricular region (e.g., on or within the coaptation structure, on or within the clip), the device can measure left ventricular pressure ("LVP"). This can provide a means of evaluating left ventricle ("LV") contractility (i.e., the rate of change of LV pressure or LV dP/dt), which is an important indicator of ventricular function. The ability of the sensor device to detect LVP can also provide an accurate measure of peak systolic arterial pressure and may serve as an indicator of aortic stenosis.

When the mitral valve repair device includes pressure sensors in both the atrial and ventricular regions, the device can be configured to monitor the differential pressure between the LV and the left atrium ("LA"). During diastole the differential pressure may provide an early indication of mitral stenosis, whereas during systole the differential pressure may provide an indication of mitral regurgitation. Careful analysis of these two measurements (i.e., LVP and LAP) over the cardiac cycle may also yield estimates of cardiac output.

In some embodiments, the mitral valve repair device may include additional or other sensors. For example, the device can include one or more accelerometers and/or one or more strain gauges that can monitor device motion and/or epicardial wall motion. As another example, the mitral valve repair device may include a microphone to detect acoustic signals in the heart, and these acoustic signals can be analyzed (e.g., via machine learning at a remote device) to provide important information regarding the function of the valves and chambers of the heart. As yet another example, the mitral valve repair device can include a flow sensor (e.g., an inductively powered flow sensor) incorporated into the atrial-facing side of the coaptation structure to measure flow patterns throughout the cardiac cycle and to detect improvement or worsening of mitral regurgitation.

Selected Embodiments of Mitral Repair Devices with Sensors

Figure 1A:
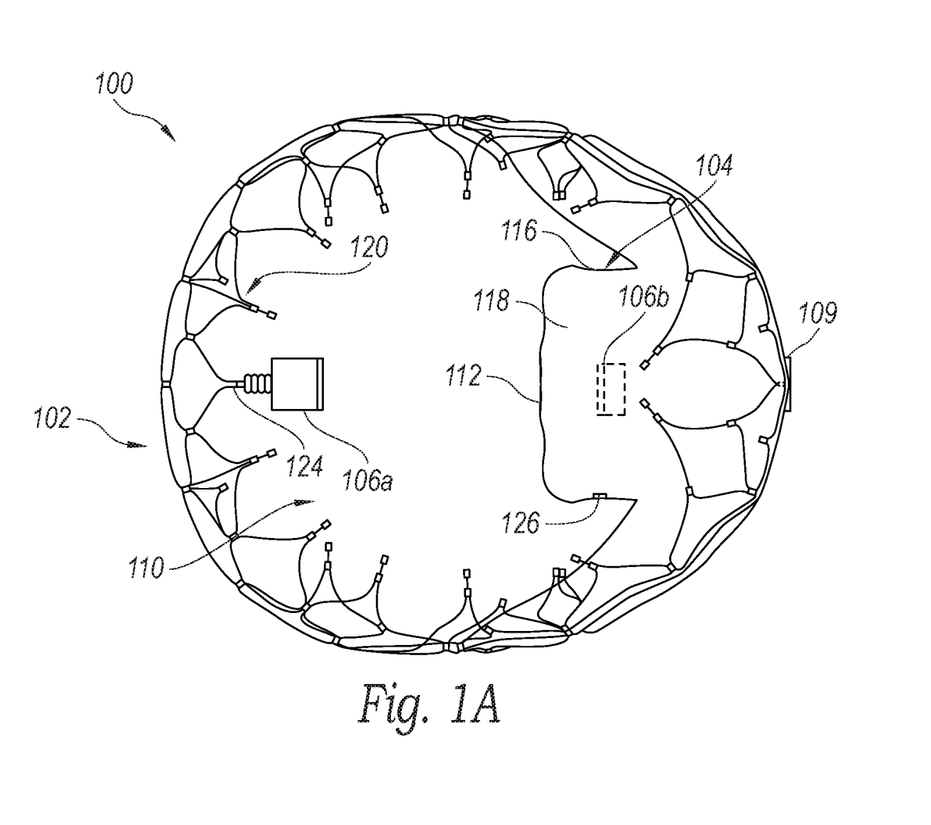
FIG. 1A is a top view of a coaptation assist device configured in accordance with some embodiments of the present technology.
Figure 1B:
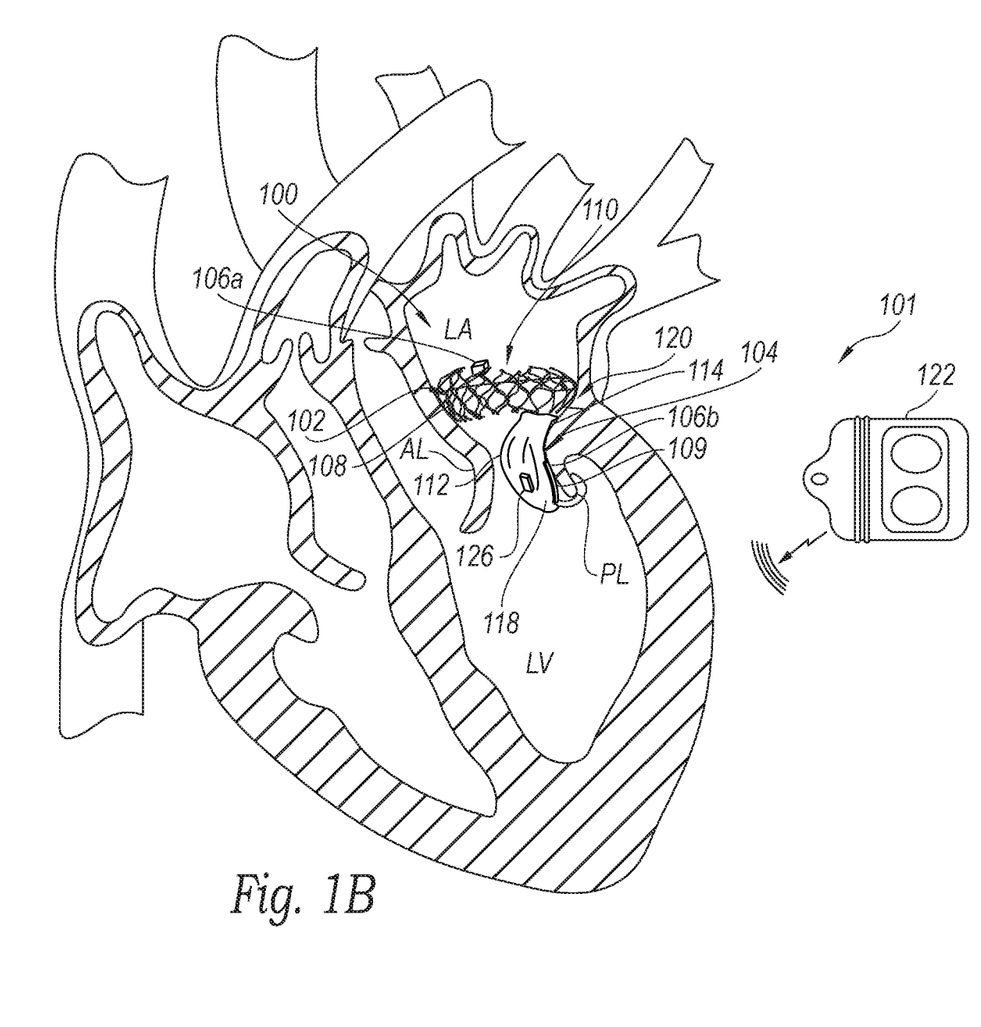
FIG. 1B illustrates a mitral valve repair and monitoring system including the coaptation assist device of FIG. 1A implanted in a heart in accordance with some embodiments of the present technology.

FIG. 1A is a top view of a coaptation assist device 100 (also referred to as a "mitral valve repair device 100" or "device 100") configured in accordance with some embodiments of the present technology, and FIG. 1B illustrates a mitral valve repair and monitoring system 101 ("system 101") including the device 100 of FIG. 1A implanted in a heart in accordance with some embodiments of the present technology. The device 100 includes a fixation member 102 (also referred to as the "atrial fixation member 102") configured to anchor the device 100 to cardiac tissue proximate to a native mitral valve annulus, a coaptation structure 104 configured to coapt with an opposing native leaflet, and at least one sensor (identified individually as a first sensor 106a and a second sensor 106b; referred to collectively as "sensors 106") for detecting one or more parameters (e.g., pressure, acceleration) associated with cardiac function and/or the functionality of the device 100. As shown in FIG. 1B, the system 101 can further include an external device 122 communicatively coupled to the sensors 106. The external device 122 can interrogate and/or power the sensors 106 to enable a clinician, technician, the patient, and/or others involved in the patient's care to monitor the patient's cardiac health and/or device performance.

The fixation member 102 can include an expandable mesh structure 108 (e.g., a stent) having an oval or circular shape in the deployed state and defining an open central lumen 110 that allows blood to pass therethrough. The mesh structure 108 can be a stent made of nitinol or other suitable stent material. As shown in FIG. 1B, the fixation member 102 can shaped to conform to the walls of the left atrium ("LA") just above the mitral annulus to secure the device 100 to the supra-annular tissue. After implantation (e.g., 3 days, 2 weeks, 1 month, 2 months), the fixation member 102 or portions thereof become covered by a layer of tissue, and this tissue ingrowth adheres the device 100 permanently to the atrial wall. The fixation member 102 may also include cleats or other frictional elements to enhance fixation and facilitate tissue ingrowth. In some embodiments, the fixation member 102 has a semi-circular or other shape that does not extend fully around the circumference of the native valve. In some embodiments, the fixation member 102 may also or alternatively include one or more portions that press against sub-annular tissue to provide sub-annular device fixation. In some embodiments, The coaptation structure 104 extends away from a portion of the fixation member 102 in generally downstream direction (along the longitudinal axis of either the central lumen 110 or the fixation member 102) and at least a portion of the coaptation structure 104 extends radially inward from the fixation member 102 into the central lumen 110 to approximate a closed position of the native leaflets. In the deployed state, the position of the coaptation structure 104 relative to the fixation member 102 is at least substantially fixed. Thus, unlike native leaflets that move back and forth to open and close the native valve, the coaptation structure 104 remains stationary during diastole and systole. The coaptation structure 104 can have an anterior portion 112 with a smooth, atraumatic surface for coapting with at least a portion of one or more native leaflets and a posterior portion 114 configured to displace and, optionally, engage at least a portion of another native leaflet. As shown in FIG. 1B, for example, the coaptation structure 104 can extend in front of the native posterior leaflet PL into the opening of the native mitral valve MV such that the anterior portion 112 is positioned to re-establish coaptation with the opposing anterior leaflet AL. The coaptation structure 104 can include struts 116 that form a frame-like structure (e.g., a mesh structure, a laser cut stent frame) and a covering 118 (e.g., a fabric) extending over at least a portion of the struts 116 to provide a smooth suitable surface for coaptation at the anterior portion 112. The covering 118 may also extend over the struts 116 along the posterior portion 114 and between the anterior and posterior portions 112, 114 in a manner that forms lateral sidewalls.

In some embodiments, the device 100 can further include one or more clips 109 that extend from the fixation member 102 in a downstream direction and/or the coaptation structure 104 to a position behind the native leaflet (e.g., the posterior leaflet PL) displaced by the coaptation structure 104. The clip 109 may grasp the native leaflet and/or engage sub-annular cardiac tissue for sub-annular stabilization of the device 100. In some embodiments, for example, the device 100 includes a clip that reaches under the central portion (i.e., P2) of the posterior leaflet PL up to the sub-annular space.

The device 100 has a first or delivery state in which the device 100 is compressed (e.g., via crimping) to a reduced cross-section for delivery to the mitral valve and a second or deployed state shown in FIGS. 1A and 1B in which the device 100 has a larger cross-section for engagement with the native valve. In some embodiments, the cross-sectional dimension of the device 100 in the delivery state is less than 20 Fr (e.g., 16-18 Fr) to facilitate intravascular delivery via a trans-septal approach.

The one or more sensors 106 can be coupled to various portions of the device 100, and the locations can be selected based upon the desired detected parameter and the type of sensor. In embodiment illustrated in FIGS. 1A and 1B, for example, the first sensor 106a is coupled to the fixation member 102 such that, after implantation, the first sensor 106a is positioned in within the left atrium LA, while the second sensor 106b is coupled to the coaptation structure 104 such that it is positioned in the left ventricle LV after implantation. In particular, the first sensor 106a is attached (e.g., welded) to an atrial crown region 120 on the anterior side of the fixation member 102, and the second sensor 106b is attached (e.g., welded) to the struts 116 of the coaptation structure 104. In the illustrated embodiment, the device 100 includes two sensors 106. In other embodiments, the device 100 can include a singular sensor 106 or more than two sensors 106.

In some embodiments the sensors 106 are pressure sensors, such as capacitive pressure sensors. Accordingly, in the configuration shown in FIGS. 1A and 1B, the first sensor 106a can measure LAP throughout the cardiac cycle and second sensor 106b can measure LVP. The external reader device 122 can establish a connection to the individual sensors 106 via an antenna associated with each sensor 106. For example, the stent frame of the fixation member 102 and the struts 116 of the coaptation structure 104 can be electroplated to define antennae for the first and second sensors 106a and 106b, respectively. Using these antennae, the external reader device 122 can communicate with the sensors 106 to obtain the detected sensor data.

Capacitive pressure sensors (e.g., capacitive micro-electro-mechanical system ("MEMS") pressure sensors) do not require batteries or electrical components and are small enough to be placed in the delivery state (e.g., crimped) with the device 100 to a diameter of 16-20 Fr. The capacitive pressure sensors function as inductive-capacitive tanks (LC tanks) and, as such, include a fixed inductive element and a capacitive element that comprises flexible plates whose separation varies with pressure. As a result, the resonant frequency of such a device varies accurately with pressure. Such capacitive pressure sensors for remote pressure monitoring (e.g., manufactured by CardioMEMs, Abbott Laboratories, Atlanta, Ga. USA) have a footprint of approximately 15 mm×2 mm×3.5 mm. A sensor of this size or smaller can fit on or within the coaptation structure 104 and/or on the atrial fixation member 102. In some embodiments, the size of the capacitive pressure sensors can be decreased considerably by placing the inductive element elsewhere in the device, such as around the fixation member 102. For example, the inductive element (e.g., a coil) can extend around the atrial edge region 120 of the fixation member 102 and/or attach to the atrial tip portions 124 of the fixation member's stent frame. This configuration is expected to enhance the exposure of the inductive element to the stimulating external field (e.g., magnetic field).

In some embodiments, the inductive element may be enhanced or optimized by using a coil with a number of low-resistance wires (e.g., gold wires). In this embodiment, the coil can be isolated from the external electromagnetic stimulating fields to prevent the stents and struts of the fixation member 102 and/or the coaptation structure 104 from acting as a Faraday cage. For example, the desired isolation can be attained by spacing the inductive element (e.g., the coil(s)) apart from a middle or central portion of the fixation member 102, such as at the top (atrial) edge of the fixation member 102 (e.g., along the atrial crown region 120). In this arrangement, the inductive element can be exposed to and stimulated by the external energy (e.g., an external magnetic field) without interference from the fixation member frame.

It is also contemplated that the inductive element of the capacitive sensor 106 is defined by the stent(s) of the fixation member 102 itself. This can be achieved by electroplating (e.g., gold-plating) the mesh structure 108 to decrease electrical resistance and increase weldability. In this embodiment, the stent of the mesh structure 108 includes two ends (e.g., formed by cutting the stent frame) at some point in its circumference to electrically isolate the portions from each other. For example, to facilitate keeping the ends electrically isolated from each other, the ends can be positioned in the location corresponding to the central region of the posterior leaflet PL where the mesh structure 108 attaches to the coaptation structure 104. The cut ends can be connected to the capacitive component of the pressure sensor.

The external device 122 (also referred to as "an external wireless reader device 122" and an "external stimulation-detection device 122") can communicate with the sensors 106 via an external antenna to interrogate the sensors 106. If the sensors 106 are capacitive sensors that detect pressure using the tank circuit (also referred to as an "LC circuit" or a "resonant circuit") described above, then the external device 122 can stimulate the circuit via an oscillating external magnetic field at a frequency close to the resonant frequency of the circuit, and the resulting tank circuit resonant frequency can then be detected via the external device 122. Since the resonant frequency is determined by the inductance and capacitance of the circuit, the detected resonant frequency can be used to determine the intracardiac pressure (e.g., processed via the external device 122 and/or other computing system). The resonant frequency of the LC circuit will be specific to the circuit components themselves, such as the specifications of the inductor, capacitor, relative positions of these features on the mitral repair device 100, and the features of the mitral repair device 100 itself. For example, in some embodiments the resonant frequency of the LC circuit may be 100 kHz to 100 MHz, with smaller inductors having higher resonant frequencies than larger inductors. If more than one tank circuit is being used (e.g., at an atrial portion of the device 100 for measuring LAP and at a ventricular portion of the device 100 for measuring LVP), the tank circuits could be designed to resonate at significantly different frequencies, which would allow both circuits (and therefore both sensors 106) to be interrogated by the external device 122 simultaneously without interfering with each other. Alternatively, the two or more circuits could be interrogated sequentially, alternating between them at predefined intervals (e.g., every 1-50 milliseconds).

In some embodiments, the external device 122 may also be used to power the sensors 106. For example, the external device 122 may include a source of radiofrequency waves, which have shown to be able to power implantable sensors even at a depth of 10 cm from a distance of 1 meter. In other embodiments, a separate external device can provide the energy source for the sensors 106.

The external stimulation-detection device 122 may be carried by or integrated into a belt worn around the patient's chest, a vest, a removable pad adhered to the patient's skin or clothing, and/or another device that can be positioned close enough to the mitral repair device 100 and transmit energy (e.g., RF waves, ultrasound) to stimulate, interrogate, detect, and/or wirelessly power the sensors 106 of the implanted device 100. In some embodiments, the external stimulation-detection device 122 may be a separate handheld device that can be used by the patient, a physician, and/or another party involved in the patient's care. The external device 122 can also include a wireless communications detector (e.g., an antenna) that communicates with the sensor 106 of the implanted mitral repair device to receive sensor data. This sensor data can be stored locally on the external device 122 and/or communicated to a separate device (e.g., a smart phone, a cloud service, another remote system). In some embodiments, the detector can be part of a device separate from the device that transmits energy to the implanted sensor.

Once the information has been detected from the one or more sensors 106, the data can be processed locally at the external device 122 and/or transmitted to a separate device (e.g., a smart phone, tablet, backend processing system, cloud, devices associated with physicians) via a communication medium (e.g., WiFi, Bluetooth, etc.) for further processing and/or communication. The raw or processed data can be used to assess various parameters associated with the patient's cardiac function (e.g., LVP, LAP) and/or functionality of the mitral repair device 100 (e.g., whether the device is operating as anticipated). This information can be conveyed to the patient via an application running on a device communicatively coupled to the system 101, such as the patient's smart phone or tablet. The information can also or alternatively be communicated to physicians and/or others to remotely track the patient. In some embodiments, the system 101 can use the tracked data to initiate alarms for the patient (e.g., via a smart phone) and/or others involved in the patient's care based on predetermined threshold parameters associated with cardiac function, overall patient health, and/or device functionality.

In various embodiments, the device 100 can include other types of sensors in addition to or in place of the capacitive sensors 106 described above. For example, the device may include a temperature sensor 126 for detecting temperature. The temperature sensor 126 can be attached to the exterior or interior of the baffle structure 104, a portion of the fixation member 102, and/or another portion of the mitral repair device 100. The temperature sensor 126 can detect temperature and/or data that can be used to determine temperature, and this information can be communicated to the external device 122 (e.g., via an antenna) for real-time monitoring of temperature surrounding the implanted mitral valve repair device 100. In further embodiments, the device 100 can also or alternatively include other sensors positioned on or integrated therein that detect other parameters associated with cardiac function, other physiological parameters, and/or device functionality.

Figure 2A:
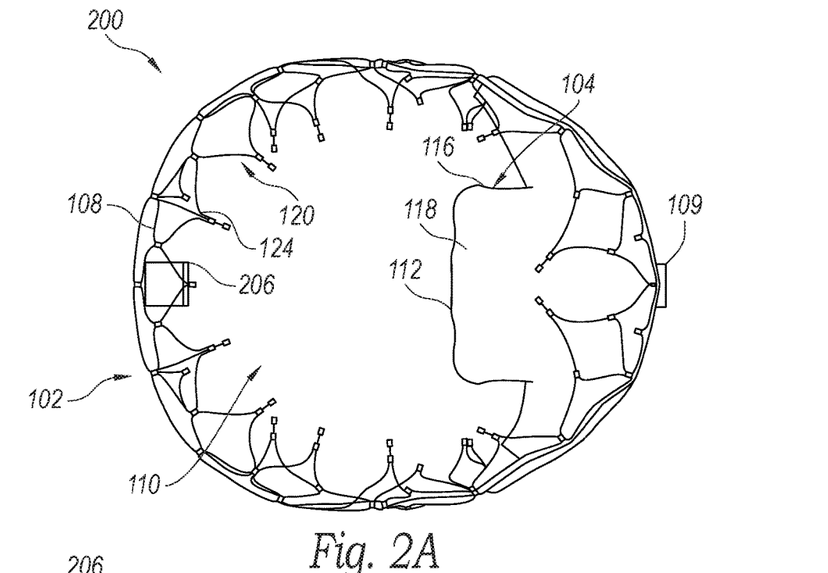
FIG. 2A is a top of a coaptation assist device configured in accordance with some embodiments of the present technology.
Figures 2B, 2C:
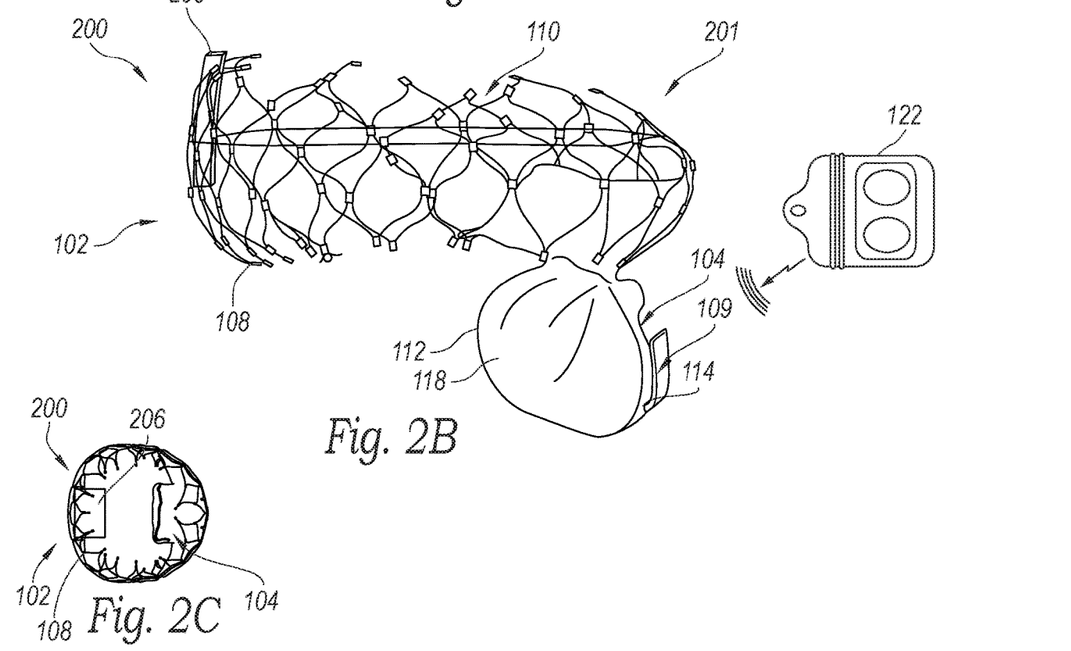
FIG. 2B is a side view of a mitral valve repair and monitoring system including the coaptation assist device of FIG. 2A in accordance with some embodiments of the present technology.
FIG. 2C is a top view of the coaptation assist device of FIG. 2A in a delivery state in accordance with some embodiments of the present technology.

FIG. 2A is a top view a coaptation assist device 200 ("device 200") configured in accordance with some embodiments of the present technology, and FIG. 2B illustrates a mitral valve repair and monitoring system 201 ("system 201") including the device 200 of FIG. 2A in accordance with some embodiments of the present technology. FIG. 2C is a top view of the device 200 of FIG. 2A in a delivery state in accordance with some embodiments of the present technology. The system 201 and the device 200 of FIGS. 2A-2C can include various features similar to the features of the system 101 and the device 100 described above with respect to FIGS. 1A and 1B. For example, the device 200 includes the fixation member 102, the coaptation structure 104, and at least one sensor 206 configured to detect one or more parameters associated with cardiac function and/or device functionality. In the embodiment illustrated in FIGS. 2A-2C, however, the sensor 206 is a self-contained sensor with more sophisticated electronic circuitry. For example, the sensor 206 may be a self-contained pressure sensor integrating both capacitive and inductive elements.

As shown in the illustrated embodiment, the self-contained sensor 206 can be attached to an anterior surface of the fixation member 102 via sutures, adhesive, welding, and/or other coupling mechanism to monitor pressure (e.g., LAP). In other embodiments, the sensor 206 can be affixed to other portions of the fixation member 102 and/or other portions of the device 200 (e.g., the coaptation structure 104). The sensor microchip and antenna can be made from biocompatible materials, allowing for long-term implantability. As would be understood to those having skill in the art, such self-contained sensors can have dimensions of approximately 15 mm×2 mm×3.5 mm. In some embodiments, the fixation member 102 can be an expanded stent cut from a 6 mm tube with a wall thickness of 0.25 mm-0.5 mm. As shown in FIG. 2C, such dimensions allow sufficient inner cross-sectional area (e.g., 5 mm inner diameter) for the sensor 206 to fit inside of the fixation member 102 when compressed to the deployment state (e.g., 18 Fr outer diameter (6 mm)). In these and other embodiments, the device 200 can include a plurality of self-contained sensors 206 coupled to various portions of the device 200 and/or one or more types of sensors (e.g., an LC circuit pressure sensor, strain gauges, microphones, flow sensors, temperature sensors).

Referring to FIG. 2B, the system 201 can further includes an element to power the device 200 and a transmitter to send detected data to the external reader device 122. The power for this system 201 can come from an inductive coil stimulated by an oscillating external magnetic field. It might alternatively come from an external ultrasonic pressure wave, or from other sources. This external power source may be integrated into the external reader device 122 or a separate external device. In some embodiments, the device 200 may include a power storage element, such as a capacitor or battery, in addition to or instead of the external power source. For example, the device 200 may store power until it has enough energy to measure via the sensor 206 and transmit via the associated antenna for a certain period of time, such as one or more heartbeats. In some embodiments, the antenna is integrated into the sensor 206. In some embodiments, the fixation member 102 or the coaptation structure 104 itself may serve as an antenna to improve transmission of the signal to the external reader device 122.

In some embodiments, the sensor 206 can include one or more surface acoustic wave ("SAW") sensors for monitoring pressure monitoring. SAW sensors have been shown to be reliable for detecting in vivo pressure measurements. In addition, the SAW sensors do not require a power source, have long term stability, are small in size, and can communicate wirelessly with external devices positioned near the sensors. Furthermore, the SAW sensor can be configured to be independently sensitive to pressure and temperature.

Figure 3A:
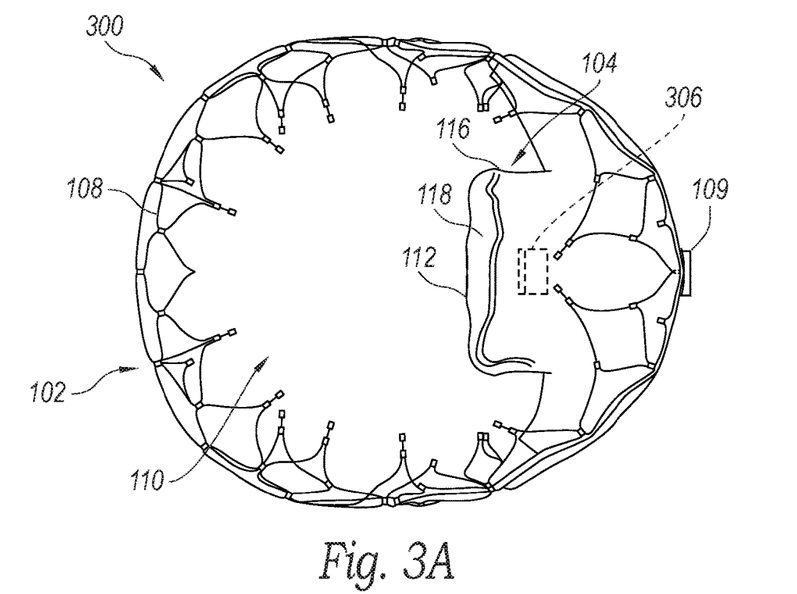
FIGS. 3A and 3B are top and side views, respectively, of a coaptation assist device configured in accordance with some embodiments of the present technology.
Figure 3B:
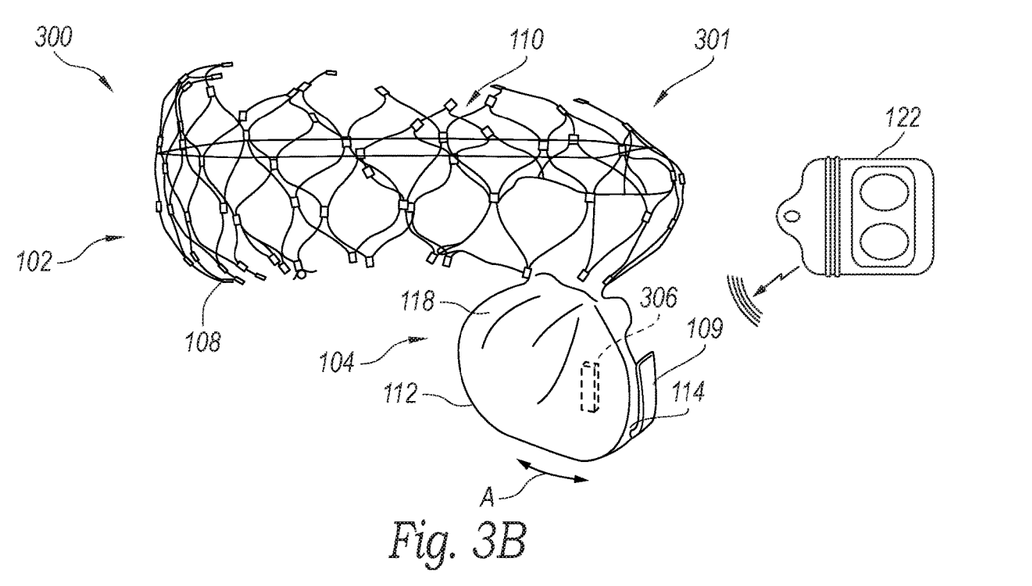

FIG. 3A is a top view a coaptation assist device 300 ("device 300") configured in accordance with some embodiments of the present technology, and FIG. 3B illustrates a mitral valve repair and monitoring system 301 ("system 301") including the device 300 of FIG. 3A in accordance with some embodiments of the present technology. The system 301 and the device 300 of FIGS. 3A and 3B can include various features similar to the features of the systems 101, 201 and the devices 100, 200 described above with respect to FIGS. 1A-2C. For example, the device 300 includes the fixation member 102, the coaptation structure 104, and at least one sensor 306. In the embodiment illustrated in FIGS. 3A and 3B, the sensor 306 includes an accelerometer for measuring device and/or cardiac motion. The accelerometer 306 can be included in the baffle structure 104 to monitor device motion and predict potential device failure or migration. For example, the accelerometer 306 may be anchored to the baffle covering 118 or baffle struts 116 (i.e., the frame of the coaptation structure 104), and be positioned within the body of the coaptation structure 104, along an outward-facing wall of the coaptation structure 104, and/or on another portion of the coaptation structure 104. In some embodiments, the accelerometer 306 may be freely positioned within the interior compartment defined by the walls of the coaptation structure 104. In this embodiment, the natural clotting that occurs within the compartment after device implantation eventually causes the free-floating accelerometer 306 to immobilize and maintain a fixed position within the coaptation structure 104. There is a small, predictable amount of motion (e.g., as indicated by arrow A) that occurs in the coaptation structure 104 throughout the cardiac cycle due to the systolic pressure load on the device 300. If this motion increases suddenly, it could be indicative of device movement or fracture. Thus, the accelerometer 306 can detect such movement to provide an early signal of potential device abnormalities to allow for early intervention before device failure.

Figure 4A:
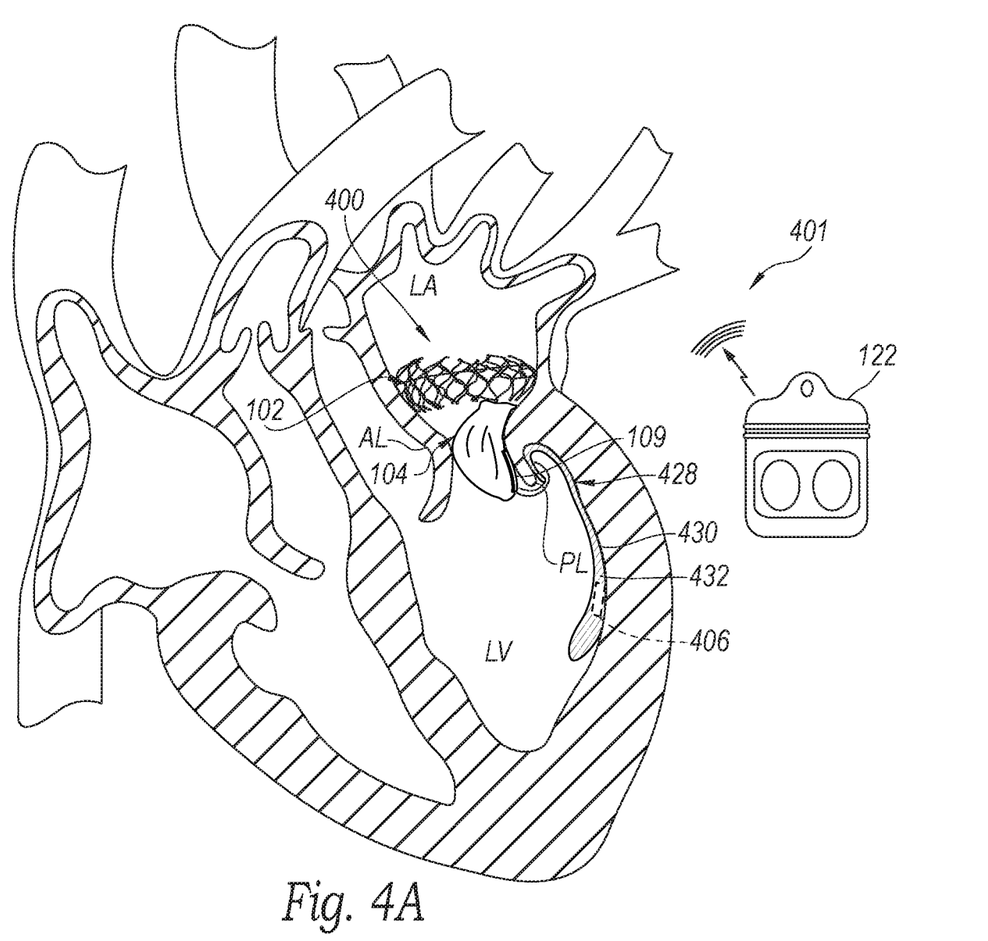
FIGS. 4A and 4B are side views of a coaptation assist device shown implanted in the heart during systole and diastole, respectively, in accordance with some embodiments of the present technology.
Figure 4B:
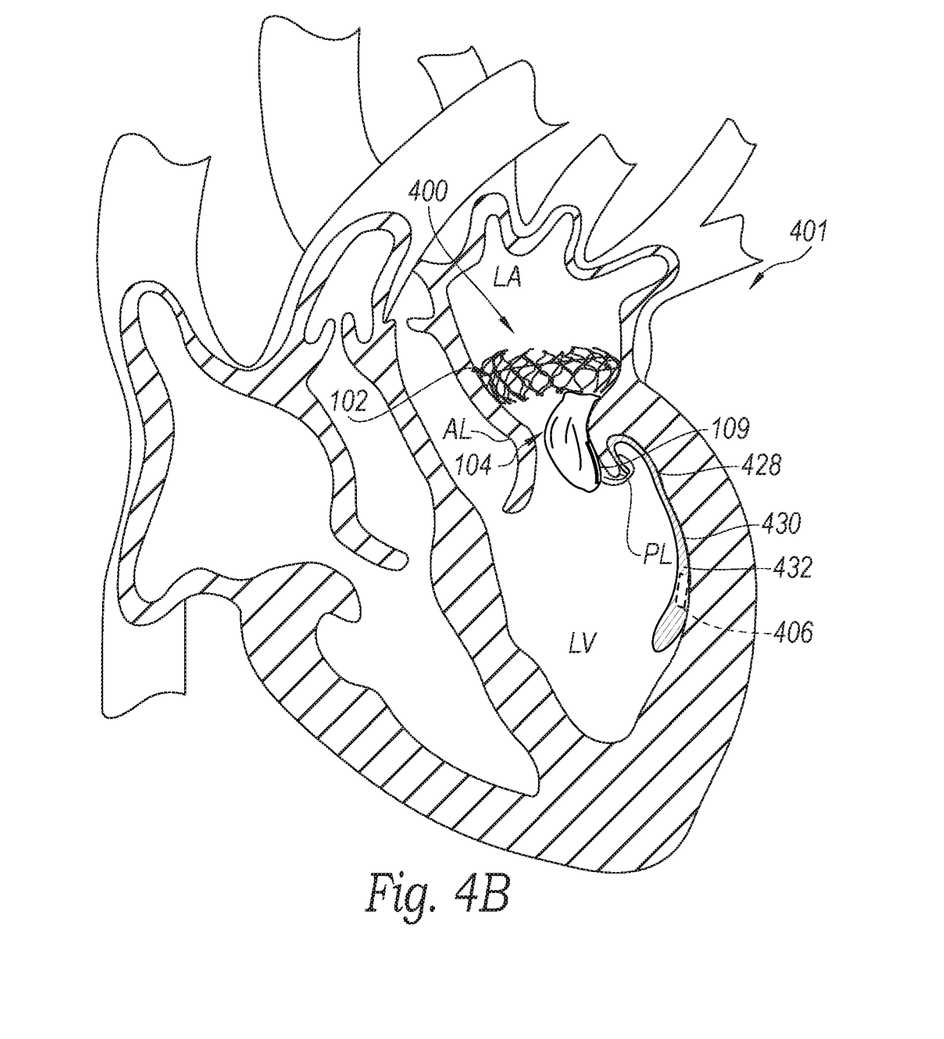

FIGS. 4A and 4B illustrate a mitral valve repair and monitoring system 401 ("system 401") including a coaptation assist device 400 ("device 400") shown implanted in a heart during systole and diastole, respectively, in accordance with some embodiments of the present technology. The system 401 and the device 400 of FIGS. 4A and 4B includes various features similar to the features of the systems 101, 201, 301 and the devices 100, 200, 300 described above with respect to FIGS. 1A-3B. For example, the device 400 includes the fixation member 102, the coaptation structure 104, and at least one sensor 406. In the embodiment illustrated in FIGS. 4A and 4B, the device 400 further includes an appendage 428 extending from the posterior side of the coaptation structure 104 or the posterior clip 109 and the sensor 406 is carried by the appendage 428. The sensor 406 may be an accelerometer that can be used to detect LV wall motion. The appendage 428 can include a flexible loop or frame structure 430 (e.g., a nitinol loop or stent structure) that is shaped to be biased outwardly away from the coaptation structure 104 such that the appendage 428 contacts or presses against the LV wall and move with the LV wall throughout the cardiac cycle. The loop/frame structure 430 can include a fabric covering 432, such as PET, to promote rapid tissue ingrowth. The accelerometer 406 can be attached to the frame structure 430, the covering 432, and/or positioned within the body of the appendage 428 such that it moves with and detects appendage movement imparted by the adjacent ventricular wall. Ventricular wall motion can be used to assess changes in ventricular function. In some embodiments, the sensor 406 is a strain gauge rather than an accelerometer, or the device 400 includes both an accelerometer and a strain gauge. The strain gauge can be affixed to the frame structure 430 and/or other portion of the appendage to detect when the cardiac wall applies force against the appendage 428. The sensor 406 can be powered wirelessly by radiofrequency waves and/or other external power source provided (e.g., the external device 122 of FIG. 1B). In other embodiments, sensor 406 can include or be coupled to a power source on the device 400 itself. In some embodiments, the device 400 can include accelerometers, strain gauges on other or additional portions of the device 400 to determine cardiac tissue movement and/or device functionality.

Figure 5A:
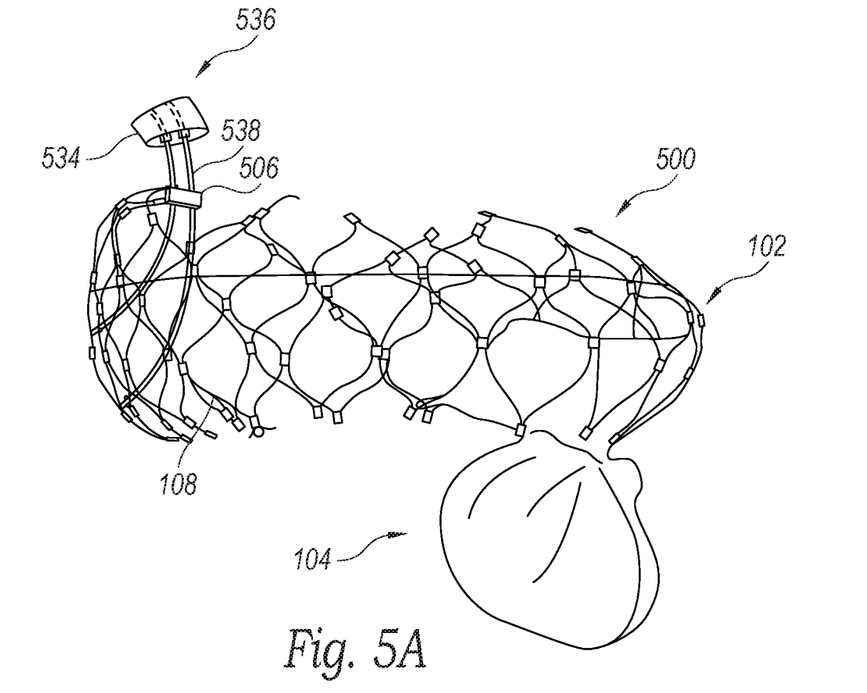
FIGS. 5A and 5B are side views of illustrating stages of a procedure for delivering a sensor to an implanted coaptation assist device in accordance with some embodiments of the present technology.
Figure 5B:
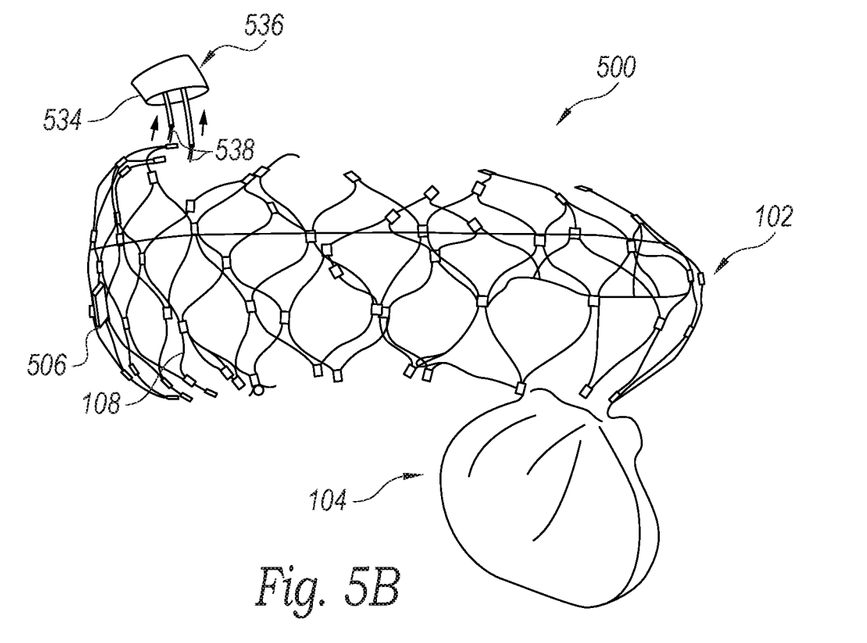

FIGS. 5A and 5B are side views of illustrating stages of a procedure for delivering a sensor 506 to an implanted coaptation assist device 500 ("device 500") in accordance with some embodiments of the present technology. The device 500 of FIGS. 5A and 5B includes various features similar to the features of the devices 100, 200, 300, 400 described above with respect to FIGS. 1A-4B. For example, the device 500 includes the fixation member 102, the coaptation structure 104, and at least one sensor 506. As described above, the sensors may be attached to or integrated with the devices before delivery such that the device and the sensor are delivered as a unit together to the target site proximate to the mitral valve. As illustrated in FIGS. 5A and 5B, however, the main body of the device 500 (e.g., the fixation member 102 and the coaptation structure 104) and the sensor 506 can be delivered sequentially. For example, to accommodate packing the device 500 into a small catheter 534 of a delivery system 536 (only distal end of catheter 534 shown), any of the sensor components described above can be deployed after the fixation member 102 and the coaptation structure 104 are already in place in the anatomy. As shown in FIG. 5A, for example, lines 538 (e.g., sutures) extending from the fixation member 102 back into the delivery system 536 can provide "rails" upon which the sensor 506 be slid and, once properly position with respect to the device 500, locked into place.

The implant devices described above can be delivered via a trans-femoral approach and/or other approach that passes the devices through the septal wall between chambers of the heart. It can also be delivered via minimally-invasive-surgical trans-apical or trans-atrial approaches, or via open surgical placement. A catheter-based delivery could take advantage of various delivery system concepts for implanting heart valve prosthesis and/or cardiac repair devices to target sites proximate to the mitral valve, the aortic valve, the tricuspid valve, and/or other portions of the heart.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A coaptation assist device for repairing a mitral valve, the coaptation assist device comprising:
   an atrial fixation member configured to press against cardiac tissue proximate to a native mitral annulus;
   a coaptation structure extending away from the atrial fixation member and radially inward from the atrial fixation member, the coaptation structure comprising an anterior surface configured to coapt with a first native leaflet during systole and a posterior surface configured to displace at least a portion of a second native leaflet, wherein the coaptation structure is substantially stationary during cardiac cycles; and
   a sensor affixed to a portion of the coaptation assist device and configured to detect one or more parameters associated with at least one of cardiac function and device functionality.

2. The coaptation assist device of claim 1 wherein:
   the sensor is a first pressure sensor coupled to the atrial fixation member and configured to detect left atrial pressure during cardiac cycles; and
   the coaptation assist device further comprises a second pressure sensor coupled to the coaptation structure and configured to detect left ventricular pressure during cardiac cycles.

3. The coaptation assist device of claim 1 wherein:
   the sensor is a first capacitive pressure sensor coupled to the atrial fixation member and configured to detect left atrial pressure during cardiac cycles, the first capacitive pressure sensor having a first LC circuit with a first resonant frequency; and
   the coaptation assist device further comprises a second capacitive pressure sensor coupled to the coaptation structure and configured to detect left ventricular pressure during cardiac cycles, the second capacitive pressure sensor having a second LC circuit with a second resonant frequency substantially different from the first resonant frequency,
   wherein the first and second LC circuits are configured to be interrogated simultaneously by an external device without interfering with each other.

4. The coaptation assist device of claim 1 wherein:
   the fixation member comprises a wire mesh structure, and wherein at least a portion of the wire mesh structure is electroplated; and
   the sensor comprises a capacitive pressure sensor attached to the wire mesh structure of the fixation member, wherein the wire mesh structure defines an antenna of the capacitive pressure sensor for transmitting and receiving signals to and from an external device.

5. The coaptation assist device of claim 1 wherein:
   the coaptation structure comprises a plurality of struts, and wherein at least a portion of the struts are electroplated; and
   the sensor comprises a capacitive pressure sensor attached to the struts of the coaptation structure, wherein the struts defines an antenna of the capacitive pressure sensor for transmitting and receiving signals to and from an external device.

6. The coaptation assist device of claim 1 wherein:
   the fixation member comprises an atrial edge region; and
   the sensor is a capacitive pressure sensor affixed to the atrial edge region, wherein the capacitive pressure sensor comprises a capacitive element and an inductive element, the inductive element is a coil extending along the atrial edge region and configured to be stimulated by an external energy source.

7. The coaptation assist device of claim 1 wherein:
   the fixation member comprises an electroplated mesh structure; and
   the sensor is a capacitive pressure sensor affixed to the fixation member, wherein the capacitive pressure sensor comprises a capacitive element and an inductive element, the electroplated mesh structure defines the inductive element.

8. The coaptation assist device of claim 1 wherein the sensor comprises a self-contained pressure sensor attached to an anterior surface of the fixation member.

9. The coaptation assist device of claim 1, further comprising a power storage element operably coupled to the sensor and configured to store energy until the power storage element has sufficient energy to detect measurements and transmit the detected measurements to an internal device.

10. The coaptation assist device of claim 1 wherein the sensor comprises an accelerometer coupled to the coaptation structure and configured to detect movement of the coaptation structure during cardiac cycles.

11. The coaptation assist device of claim 1 wherein the coaptation structure comprises a plurality of struts that define a chamber, and wherein, before device delivery, the sensor is positioned freely within the chamber.

12. The coaptation assist device of claim 1, further comprising:
   an appendage extending from a posterior portion of the coaptation structure, the appendage comprises a flexible frame biased outwardly away from the coaptation structure and configured to contact a left ventricular wall; and
   wherein the sensor comprises an accelerometer attached to the appendage to detect movement of the left ventricular wall.

13. The coaptation assist device of claim 1 wherein the sensor comprises at least one of an accelerometer and a strain gauge configured to detect cardiac wall movement.

14. The coaptation assist device of claim 1 wherein the sensor comprises a microphone configured to detect acoustic signals during cardiac cycles.

15. The coaptation assist device of claim 1 wherein the sensor comprises at least one flow sensor coupled to an atrial-facing surface of the coaptation structure and configured to measure flow patterns throughout cardiac cycles.

16. A heart valve repair and monitoring system, comprising:
   a valve repair device comprising— a coaptation structure comprising an anterior surface configured to coapt with a first native leaflet during systole and a posterior surface configured to displace at least a portion of a second native leaflet; and a fixation member coupled to the coaptation structure and configured to anchor the coaptation structure proximate to a native heart valve annulus, wherein the coaptation structure remains substantially stationary relative to the fixation member during cardiac cycles; and a pressure sensor configured to detect pressure during cardiac cycles; and an external stimulation-detection device configured to interrogate the pressure sensor to wirelessly receive detected data.

17. The heart valve repair and monitoring system of claim 16 wherein the external stimulation-detection device is configured to power the pressure sensor.

18. The heart valve repair and monitoring system of claim 16 wherein:

the pressure sensor is a first capacitive pressure sensor coupled to the fixation member and configured to detect left atrial pressure during cardiac cycles, the first capacitive pressure sensor having a first LC circuit with a first resonant frequency; and the valve repair device further comprises a second capacitive pressure sensor coupled to the coaptation structure and configured to detect left ventricular pressure during cardiac cycles, the second capacitive pressure sensor having a second LC circuit with a second resonant frequency substantially different from the first resonant frequency, wherein the first and second LC circuits are configured to be interrogated simultaneously by an external device without interfering with each other.

19. The heart valve repair and monitoring system of claim 18 wherein:

the first capacitive pressure sensor comprises a first LC circuit with a first resonant frequency;

the second capacitive pressure sensor comprises a second LC circuit with a second resonant frequency substantially different from the first resonant frequency, the external stimulation-detection device is configured to simultaneously interrogate the first and second LC circuits.

20. The heart valve repair and monitoring system of claim 16, further comprising:

a delivery system configured to deliver the sensor to the fixation member after the fixation member is deployed.

21. The heart valve repair and monitoring system of claim 16 wherein:

the fixation member comprises a wire mesh structure;

the coaptation structure comprises a plurality of struts; and at least one of the wire mesh structure and the plurality of struts define an antenna for the pressure sensor for communication with the external stimulation-detection device.

22. The heart valve repair and monitoring system of claim 16, further comprising an accelerometer coupled to the coaptation structure and configured to detect movement of the coaptation structure during cardiac cycles.

23. The heart valve repair and monitoring system of claim 16 wherein the valve repair device comprises:

an appendage extending from a posterior portion of the coaptation structure, the appendage being biased outwardly away from the coaptation structure and configured to contact a ventricular wall; and an accelerometer attached to the appendage to detect movement of the ventricular wall during cardiac cycles.

24. The coaptation assist device of claim 1 wherein the atrial fixation member extends at least partially about a longitudinal axis, and wherein the coaptation structure extends away from the atrial fixation member and radially inward from the atrial fixation member such that the anterior surface is positioned closer to the longitudinal axis than the atrial fixation member.

* * * * *